United States Patent
Roberts et al.

(10) Patent No.: US 9,061,106 B2
(45) Date of Patent: Jun. 23, 2015

(54) SAFETY DEVICE FOR A PRE-FILLED SYRINGE AND AN INJECTION DEVICE

(75) Inventors: Gareth Roberts, Wrexham (GB); Matthew Ekman, Cheshire (GB)

(73) Assignee: SANOFI-AVENTIS DEUTSCHLAND GMBH, Frankfurt am Main (DE)

( * ) Notice: Subject to any disclaimer, the term of this patent is extended or adjusted under 35 U.S.C. 154(b) by 218 days.

(21) Appl. No.: 13/997,372

(22) PCT Filed: Dec. 30, 2011

(86) PCT No.: PCT/EP2011/074276
§ 371 (c)(1),
(2), (4) Date: Jun. 24, 2013

(87) PCT Pub. No.: WO2012/093071
PCT Pub. Date: Jul. 12, 2012

(65) Prior Publication Data
US 2013/0296798 A1    Nov. 7, 2013

(30) Foreign Application Priority Data
Jan. 4, 2011    (EP) .................................... 11150078

(51) Int. Cl.
*A61M 5/32*    (2006.01)
*A61M 5/28*    (2006.01)

(52) U.S. Cl.
CPC ................. *A61M 5/326* (2013.01); *A61M 5/28* (2013.01); *A61M 2005/3261* (2013.01); *A61M 2005/3263* (2013.01); *A61M 2005/3267* (2013.01)

(58) Field of Classification Search
CPC ............. A61M 2005/3261; A61M 2005/3263; A61M 2005/3267; A61M 5/28; A61M 5/326
See application file for complete search history.

(56) References Cited

U.S. PATENT DOCUMENTS

2010/0137809 A1*    6/2010    Tschirren et al. ............. 604/187

FOREIGN PATENT DOCUMENTS

| EP | 1208862 | 5/2002 |
|---|---|---|
| EP | 2090326 | 8/2009 |
| GB | 2447787 | 9/2008 |
| WO | 2006/111861 | 10/2006 |

OTHER PUBLICATIONS

International Search Report for Int. App. No. PCT/EP2011/074276, completed Mar. 26, 2012.

* cited by examiner

*Primary Examiner* — Rebecca E Eisenberg
(74) *Attorney, Agent, or Firm* — McDonnell Boehnen Hulbert & Berghoff LLP

(57) ABSTRACT

According to the invention, a safety device for a pre-filled syringe comprises of a support body adapted to mount the pre-filled syringe, a first needle shield slidably arranged with respect to the support body and a second needle shield slidably arranged with respect to the support body and releasably retained in a retracted position (PR). A proximal movement of the first needle shield with respect to the support body releases the retention of the second needle shield in the retracted position (PR), so that the second needle shield is allowed to slide in the distal direction towards an advanced position (PA).

9 Claims, 9 Drawing Sheets

SAFETY DEVICE FOR A PRE-FILLED SYRINGE AND AN INJECTION DEVICE

CROSS REFERENCE TO RELATED APPLICATIONS

The present application is a U.S. National Phase Application pursuant to 35 U.S.C. §371 of International Application No. PCT/EP2011/074276 filed Dec. 30, 2011, which claims priority to European Patent Application No. 11150078.1 filed Jan. 4, 2011. The entire disclosure contents of these applications are herewith incorporated by reference into the present application.

TECHNICAL FIELD

The present invention relates to safety devices that provide needle safety and more particularly to safety devices for pre-filled syringes. The safety device is adapted to avoid accidental needle pricks and needle injuries before, during and after an injection of a medication or drug contained in the pre-filled syringe. In particular, the safety device provides needle safety for a subcutaneous self-administrated injection or for an injection administered by a health-care professional. The present invention further relates to injection devices comprising a pre-filled syringe.

BACKGROUND

Pre-filled syringes that are filled with a selected dosage of a medication are well known injection devices for administering the medication to a patient. Safety devices for covering a needle of a pre-filled syringe before and after use are also well known. Typically, these devices comprise a needle shield that is either manually moved or moved by the action of a relaxing spring to surround the needle.

A different type of safety device known in the state of the art achieves the object of providing needle safety by arranging the pre-filled syringe movable relative to a body, where the pre-filled syringe is retracted into the body after the injection.

SUMMARY

It is an object of the present invention to provide an improved safety device for a pre-filled syringe.

It is a further object of the invention to provide an improved injection device comprising a pre-filled syringe that is safe to handle and in particular prevents accidental needle stick injuries.

The object is achieved by a safety device according to claim 1 and by an injection device according to claim 9.

Preferred embodiments of the invention are given in the dependent claims.

In the context of this specification, the terms distal and proximal are defined from the point of view of a person performing an injection. Consequently, a distal direction refers to a direction pointing towards the body of a patient receiving an injection and a distal end defines an end of an element that is directed towards the body of the patient. Respectively, the proximal end of an element or the proximal direction is directed away from the body of the patient receiving the injection and opposite to the distal end or distal direction.

According to the invention, a safety device for a pre-filled syringe comprises a support body adapted to mount the pre-filled syringe, a first needle shield slidably arranged with respect to the support body and a second needle shield slidably arranged with respect to the support body and releasably retained in a retracted position.

A proximal movement of the first needle shield with respect to the support body releases the retention of the second needle shield in the retracted position, so that the second needle shield is allowed to slide in the distal direction towards an advanced position.

The safety device provides needle safety for an injection needle of the pre-filled syringe that is mounted to the support body. Typically, a bi-directional movement is required from a needle sleeve to cover and to expose the injection needle. According to the invention, needle safety is provided by a tubular needle sleeve that is split into two parts, namely the first and the second needle shield that are allowed to move in opposite directions with respect to the support body. In particular, the first needle shield is allowed to move proximally from an initial first position to second position, whereas the second needle shield is allowed to move distally from the retracted position to the advanced position.

The proximal movement of the first needle shield from the first to the second position triggers the release of the second needle shield, so that the second needle shield is allowed to slide distally from the retracted to the advanced position to cover the injection needle after an injection has been carried out. The release of the second needle shield thus activates the safety features of the safety device preventing accidental needle stick injuries after the injection. The safety device is easy to use and the safety features are particularly intuitive to activate by simply pressing the safety device towards the skin of the patient, whereby the first needle shield is pushed proximally to release the second needle shield.

According to one possible embodiment of the invention, the first needle shield comprises a first flange and the second needle shield comprises a second flange. The first and the second flange are adapted to rest on the skin of a patient. Both the first and the second flange provide a contact surface of increased area to reduce the pressure exerted upon the skin of the patient during the injection.

The second needle shield may comprise a helical recess accommodating a projection of the support body. The interaction of the helical recess with the projection forces the second needle shield to rotate with respect to the support body when the second needle shield is translated parallel to a central axis of the safety device. The rotation slows down the distal movement of the second needle shield and may further reduce the pressure exerted upon a skin surface of the patient by a spring-driven first or second needle shield.

The use of two independent parts to provide needle safety alleviates manufacturing requirements, as the first and the second needle shield may be biased and/or driven by separate power sources. According to another possible embodiment of the invention, a spring means biases the second needle shield in the distal direction towards the advanced position. Consequently, the spring means is only required to exert a force in a single direction. This allows for a use of alternative spring means as power sources that may be economically mass produced.

The spring means may be designed as a torsion spring that exerts a torque upon the second needle shield. The guidance of the projection of the support body within the helical recess of the second needle shield couples the rotation of the second needle shield to a translatory movement in the distal direction. As the safety device is provided with a split needle shield comprising the first and the second needle shield, the torsion spring is only required to relax once, whereby the second needle shield is moved distally to cover the injection needle. The safety device is designed as a non-reusable device that is disposed after it has been used in a single injection to minimize the risk of infections caused by used injection needles.

Preferably, the first and the second needle shield are made from plastics materials that are inexpensive to produce. The first needle shield is made from an opaque or transparent plastics material and the second needle shield is made from an opaque or transparent plastics material. According to possible embodiments of the invention, the safety device is manufactured from a combination of opaque and transparent plastics materials. In particular, the first needle shield may be made from a transparent material to alleviate the insertion of the injection needle into the skin of the patient, whereas the second needle shield may be made from an opaque material that hides the injection needle from the view of the patient after the injection. Alternatively, different combinations of opaque and transparent material choices are within the scope of the present invention. For example, the first needle shield may be made from an opaque material to hide the injection needle before an injection. This may help a user of the safety device suffering from a fear of needles in self-administering a dose of medication contained in the pre-filled syringe.

The safety device comprises an outer body that is slidably arranged with respect to the support body. The outer body is manually actuated to expel the dose of medication contained in the pre-filled syringe through the injection needle. A first protrusion of the support body engages a recess of the outer body to provide a mechanical resistance that is adapted to a resistance or friction occurring between the first needle shield and the support body. In particular, the mechanical resistance is adapted in a manner that prevents a distal movement of the outer body with respect to the support body until the first needle shield is moved to second position. This prevents so-called wet injections and a spilling of medication before the injection needle is inserted into the skin of the patient.

The second needle shield projects distally from the support body in the advanced position and surrounds the injection needle of the pre-filled syringe mounted to the support body. The support body comprises first and second catches that engage and lock the second needle shield in the advanced position. After a single injection has been performed, the second needle shield is permanently locked to the advanced position. Thus, accidental needle stick injuries are efficiently prevented.

According to the invention, an injection device comprises a safety device and a pre-filled syringe with an injection needle. The safety device comprises a support body adapted to mount the pre-filled syringe, a first needle shield slidably arranged with respect to the support body and a second needle shield slidably arranged with respect to the support body and releasably retained in a retracted position.

A proximal movement of the first needle shield with respect to the support body releases the retention of the second needle shield in the retracted position, so that the second needle shield is allowed to slide in the distal direction towards an advanced position.

The injection device comprising the pre-filled syringe and the safety device combines the aforementioned advantages and avoids inadvertent needle sticks injuries. The injection device is cheap to manufacture and is disposed after a single injection has been carried out.

The injection device is well suited to be used for self-administered injections and for injections performed by a health care professional. Consequently, the person referred to as the patient or the user may be one and the same person.

The spring means is capable of moving the second needle shield from the retracted position to the advanced position. The injection needle is surrounded by the second needle shield in the advanced position. Upon removal of the injection device from the injection site, the spring means relaxes and moves the second needle shield in the advanced position. A separate interaction to ensure needle safety after the injection is not required from the user.

The pre-filled syringe may be filled with a medicament.

The term "medication", or "drug", or "medicament", as used herein, means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des (B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyhepta¬ decanoyl) human insulin.

Exendin-4 for example means Exendin-4(1-39), a peptide of the sequence H His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:
H-(Lys)4-des Pro36, des Pro37 Exendin-4(1-39)-NH2,
H-(Lys)5-des Pro36, des Pro37 Exendin-4(1-39)-NH2,
des Pro36 Exendin-4(1-39),
des Pro36 [Asp28] Exendin-4(1-39), des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39),
wherein the group -Lys6-NH2 may be bound to the C-terminus of the Exendin-4 derivative;
or an Exendin-4 derivative of the sequence
des Pro36 Exendin-4(1-39)-Lys6-NH2 (AVE0010),
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro37, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-desAsp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25] Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp(O2)25, Asp28] Exendin-4(1-39)-NH2,
des Pro36, Pro37, Pro38 [Met(O)14, Trp(O2)25, Asp28] Exendin-4(1-39)-(Lys)6-NH2,
H-(Lys)6-des Pro36, Pro37, Pro38 [Met(O)14, Trp(O2)25, Asp28] Exendin-4(S1-39)-(Lys)6-NH2,
H-Asn-(Glu)5-des Pro36, Pro37, Pro38 [Met(O)14, Trp(O2)25, Asp28] Exendin-4(1-39)-(Lys)6-NH2;
or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by $\alpha, \delta, \epsilon, \gamma$, and $\mu$. The type of heavy chain present defines the isotype of antibody; these chains are found in IgA, IgD, IgE, IgG, and IgM antibodies, respectively.

Distinct heavy chains differ in size and composition; $\alpha$ and $\gamma$ contain approximately 450 amino acids and $\delta$ approximately 500 amino acids, while $\mu$ and $\epsilon$ have approximately 550 amino acids. Each heavy chain has two regions, the constant region (CH) and the variable region (VH). In one species, the constant region is essentially identical in all antibodies of the same isotype, but differs in antibodies of different isotypes. Heavy chains $\gamma$, $\alpha$ and $\delta$ have a constant region composed of three tandem Ig domains, and a hinge region for added flexibility; heavy chains $\mu$ and $\epsilon$ have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H-H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1 C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will be better understood from the detailed description given in the following. The accompanying drawings are given for illustrative purposes only and do not limit the scope of the present invention.

Corresponding parts are marked with the same reference symbols in all figures.

DETAILED DESCRIPTION

Figure 1:
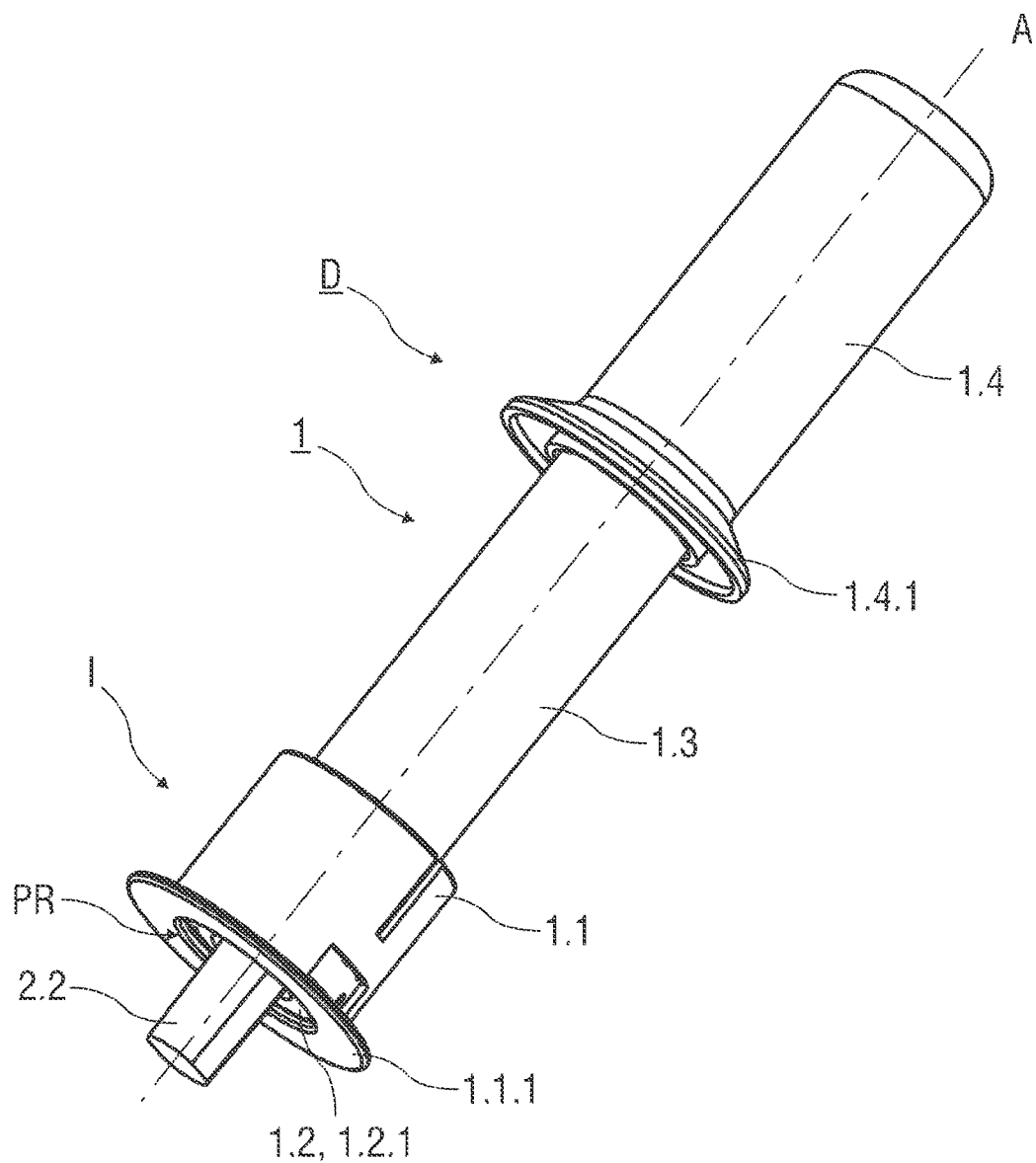
FIG. 1 shows a perspective view of the injection device according to the invention before use.

FIG. 1 shows a perspective view of an injection device D with a safety device 1 for a pre-filled syringe 2 as it would be presented to a user performing an injection. The safety device 1 comprises a substantially cylindrical and hollow first needle shield 1.1 and a substantially cylindrical and hollow second needle shield 1.2. The first and the second needle shield 1.1, 1.2 are slidably arranged with respect to a support body 1.3 that receives and mounts the pre-filled syringe 2. The first and the second needle shield 1.1, 1.2 are allowed to move in opposite directions with respect to the support body 1.3.

Before usage of the safety device 1, the first needle shield 1.1 is initially retained in a first position I, wherein the first needle shield 1.1 protrudes the support body 1.2 in a distal direction, whereas the second needle shield 12 is substantially received within the support body 1.2 in a retracted position PR.

According to the embodiment of the invention shown in FIG. 1, the first needle shield 1.1 slides over the support body 1.3, whereas the second needle shield 1.2 slides within the support body 1.3. Alternatively, the first needle shield 1.1 may slide within the support body 1.3, whereas the second needle shield 1.2 may comprise dimensions that allows the second needle shield 1.2 to slide over an outer surface of the support body 1.3.

The first needle shield 1.1 comprises a circumferential and radial protruding first flange 1.1.1 and the second needle shield 1.1, 1.2 comprises a circumferential second flange 1.2.1. The first and the second flange 1.1.1, 1.2.1 are adapted to bear against the skin of a patient during the injection. Edges of the first and the second flange 1.1.1 that may touch the skin of the patient are rounded to avoid injuries. Both the first and the second flange 1.1.1, 1.2.1 have central openings centred on the central axis A of the safety device 1. The first and the second flange 1.1.1, 1.2.1 may be integrally formed to the respective first or second needle shield 1.1, 1.2. Alternatively, the first or the flange 1.1.1, 1.2.1 may be designed as a separate part a made from a plastics material that is attached to the respective first or second needle shield 1.1, 1.2.

The second needle shield 1.2 is releasably retained in the retracted position PR. A proximal movement of the first needle shield 1.1 triggers the release of the second needle shield 1.2 and thus the activation of the safety features of the safety device 1.

FIG. 1 shows the safety device 1 comprising an essentially cylindrical and hollow outer body 1.4 with an open distal and a closed proximal end. The proximal end of the support body 1.3 is received within the open distal end of the outer body 1.4. The outer body 1.4 is slidably arranged with respect to the support body 1.3 and may slide in a distal direction to substantially receive the support body 1.3 at the end of an injection stroke.

A circumferential and outwardly protruding support flange 1.4.1 is integrally formed to an outer surface of the outer body 1.4 close to its distal end. The outer body 1.4 is adapted to be gripped and pushed by a user in the distal direction, whereby the support flange 1.4.1 supports the hand of the user performing the injection stroke.

Preferably, the first and the second needle shield 1.1, 1.2, the support body 1.3 and the outer body 1.4 are made from a plastics material. The first and/or the second needle shield 1.1, 1.2 may be made from an opaque plastics material to hide the injection needle 2.1 of the pre-filled syringe 2 from the view of a patient throughout the injection. This may help to ease a possible fear of needles of the patient. Alternatively, the first and/or the second needle shield 1.1, 1.2 may be made from a transparent plastic material, so that the user may visually confirm the correct placement of the injection needle 2.1 and easily insert the injection needle 2.1 into the skin of the patient.

According to a possible embodiment of the invention, the first needle shield 1.1 is made from a transparent material to ease the insertion of the injection needle 2.1 into the skin of the patient, whereas the second needle shield 1.2 covering the injection needle 2.1 after the injection is made from an opaque plastic material.

In the packaged state shown in FIG. 1, the injection needle 2.1 of the pre-filled syringe 2 is covered by a needle cap 2.2. Preferably, the needle cap 2.2 is at least partially made from a plastics material like rubber. The needle cap 2.2 protrudes the first flange 1.1.1 in the distal direction, so that the user can easily remove the needle cap 2.2 before an injection is performed.

Figure 2:
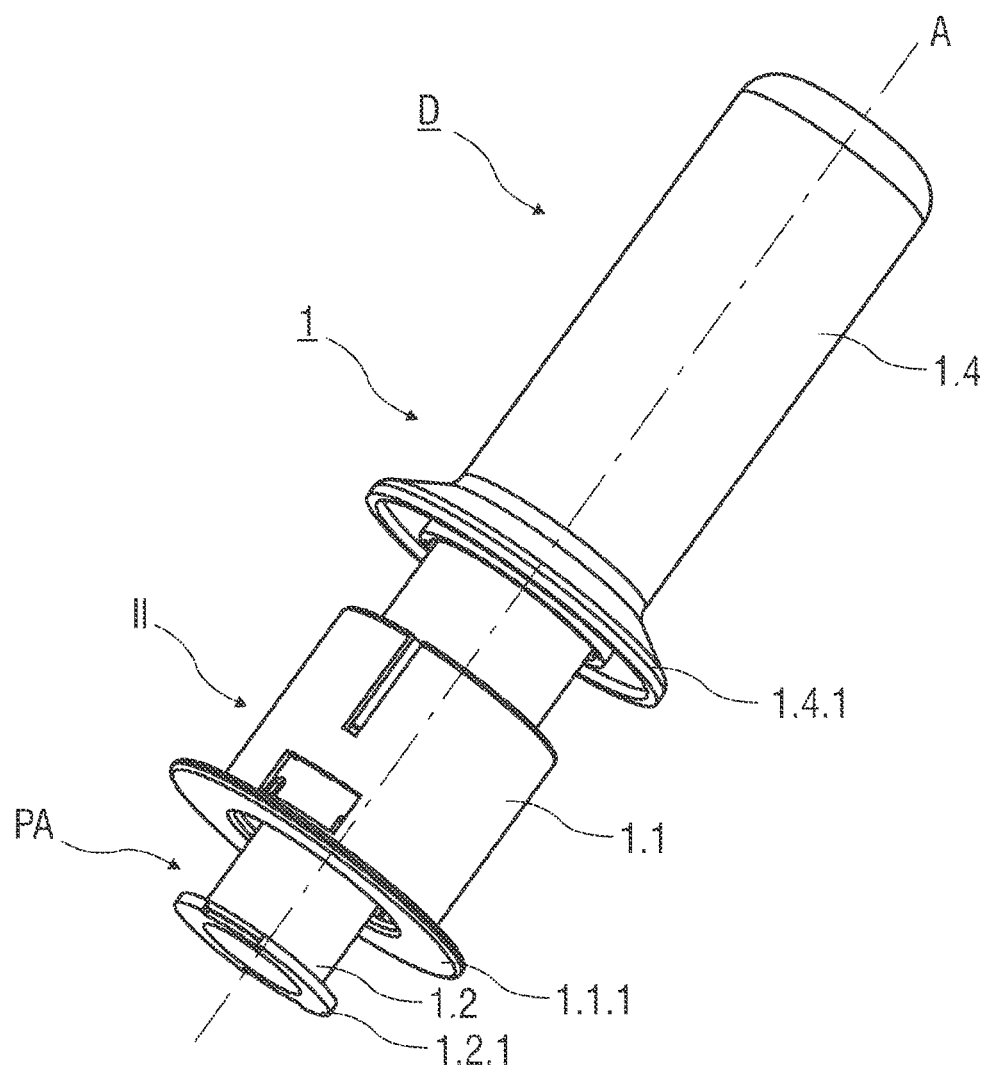
FIG. 2 shows a perspective view of the injection device in a needle safe state after use.

FIG. 2 shows a perspective view of the injection device D after an injection has been carried out. The support body 1.3 is substantially received within the hollow outer body 1.4. The first needle shield 1.1 is arranged in a second position II, wherein the first needle shield 1.3 is refracted in the proximal direction.

After use of the injection device D, the second needle shield 1.2 is locked to an advanced position PA, wherein the needle shield 1.2 protrudes the support body 1.3 in the distal direction to ensure needle safety.

Figure 3:
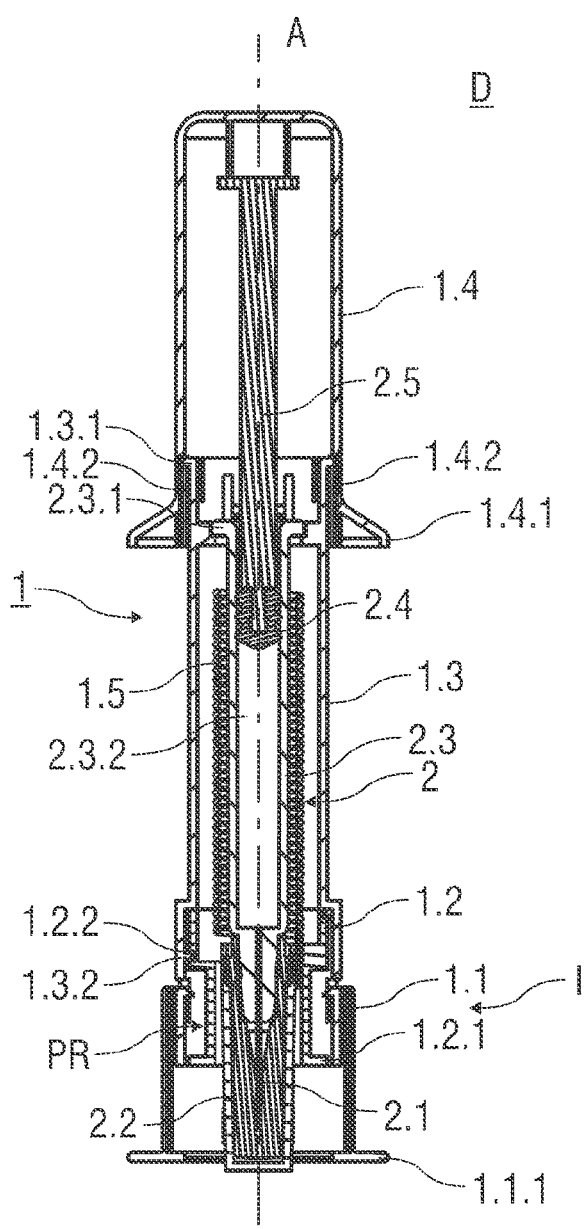
FIG. 3 shows a sectional view of the injection device before use.

FIG. 3 shows a sectional view of the injection device D before use. The needle cap 2.2 is frictionally attached to a barrel 2.3 of the pre-filled syringe 2 to cover the injection needle 2.1 before use. The pre-filled syringe 2 is mounted to the support body 1.3 by a mechanical connection that may in particular engage a proximal barrel collar 2.3.1 of the barrel 2.3. The barrel collar 2.3.2 of the pre-filled syringe 2 is attached to the support body 1.3 by a clip connection.

An inner cavity 2.3.2 of the pre-filled syringe 2 contains a dose of medication or drug. A stopper 2.4 that is connected to a plunger 2.5 fluid-tightly seals a proximal end of the inner cavity 2.3.2. The stopper 2.4 may be moved by pushing the plunger 2.5 in the distal direction to expel the dose of medication through the injection needle 2.1. The plunger 2.5 is attached to or abuts an inner surface of the outer body 1.4, so that the plunger 2.5 and the stopper 2.4 connected thereto may be moved by pushing the outer body 1.4 with respect to the support body 1.3 in the distal direction.

The support body 1.3 comprises a first protrusion 1.3.1 that projects radial outwards from a proximal end of the support body 1.3 into a recess 1.4.2 formed into an inner surface of the outer body 1.4. The first protrusion 1.3.1 may be deflected radially inwards to disengage the recess 1.4.2 when the outer body 1.4 is pushed with respect to the support body 1.3 by a sufficiently large force. The interaction of the first protrusion 1.3.1 and the recess 1.4.2 provides a mechanical resistance that prevents the outer body 1.4 from being accidentally moved in the distal direction, so that an inadvertent spilling of medication is avoided.

The mechanical resistance provided by the interaction of the first protrusion 1.3.1 and the recess 1.4.2 is adapted to a resistance or friction that is required to be overcome when the first needle shield 1.1 is slid from the first position I to the second position II. This ensures that the first needle shield 1.1 is refracted in the second position II and the injection needle 2.1 is inserted into the skin surface of the patient before the outer body 1.4 is moved to expel the dose of medication through the injection needle 2.1.

A spring means 1.5 is arranged within the support body 1.3 that biases the second needle shield 1.2 in the distal direction. According to a possible embodiment of the invention, the spring means 1.5 is designed as a torsion spring that exerts a torque upon the second needle shield 1.2. Alternatively, the spring means 1.5 may be designed as a compression spring that exerts a linear biasing force upon the second needle shield 1.2.

Before the injection is performed, the second needle shield 1.2 is releasably retained within the support body 1.3 in the retracted position PR. As shown in FIG. 3 and in more detail in FIG. 4, a helical recess 1.2.2 is formed into an outer surface of the substantially cylindrical second needle shield 1.2. The helical recess 1.2.2 accommodates a projection 1.3.2 projecting radial inwards from the support body 1.3. Upon release, the needle shield 1.2 moves parallel to the central axis A in the distal direction, whereby the projection 1.3.2 is guided along the helical recess 1.2.2, so that the second needle shield 1.2 is forced to rotate around the central axis A.

Figure 4:
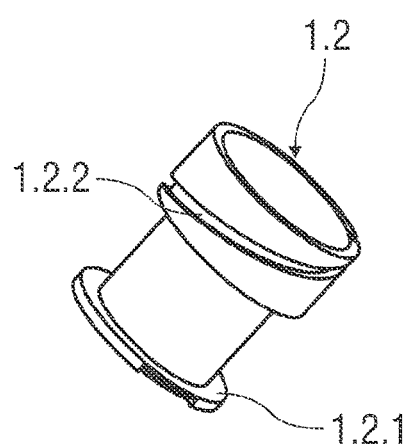
FIG. 4 shows a perspective view of a second needle shield.

FIG. 4 shows the second needle shield 1.2 with the helical recess 1.2.2 formed into the outer surface thereof in a perspective view.

Figure 5A:
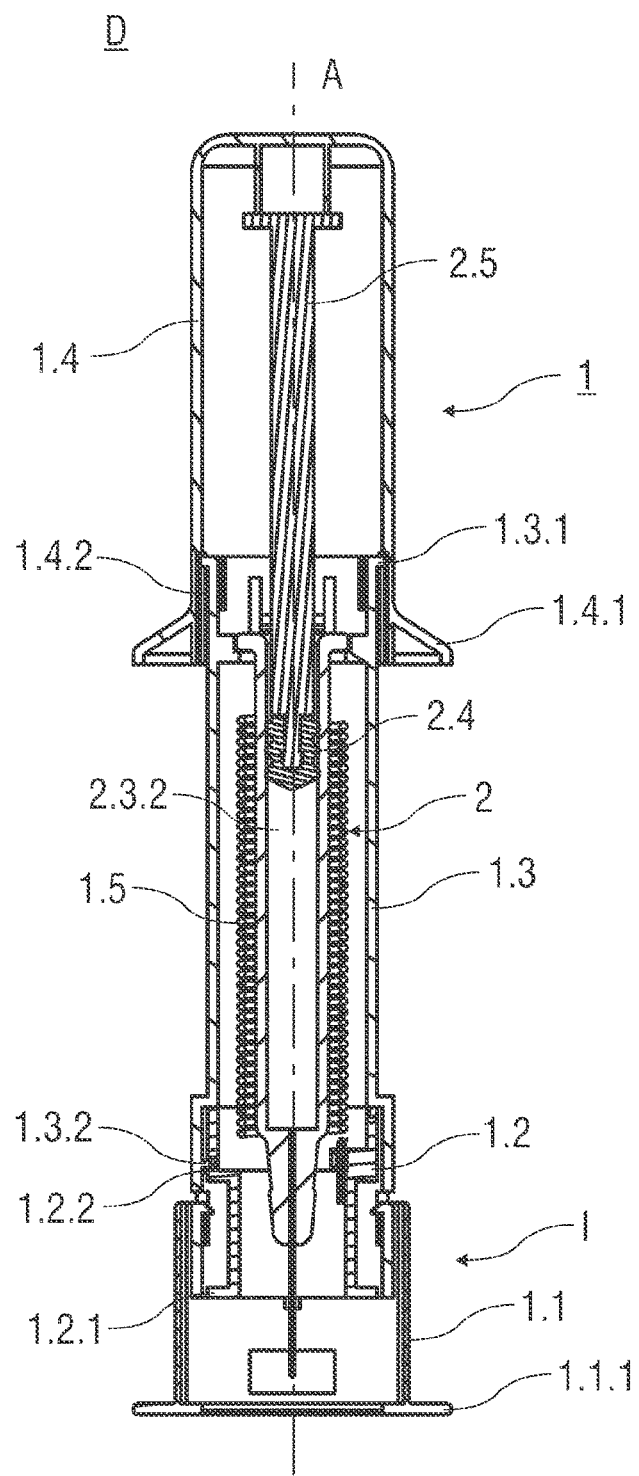
FIGS. 5A and 5B shows two different sectional views of the injection device before an injection is performed.
Figure 5B:
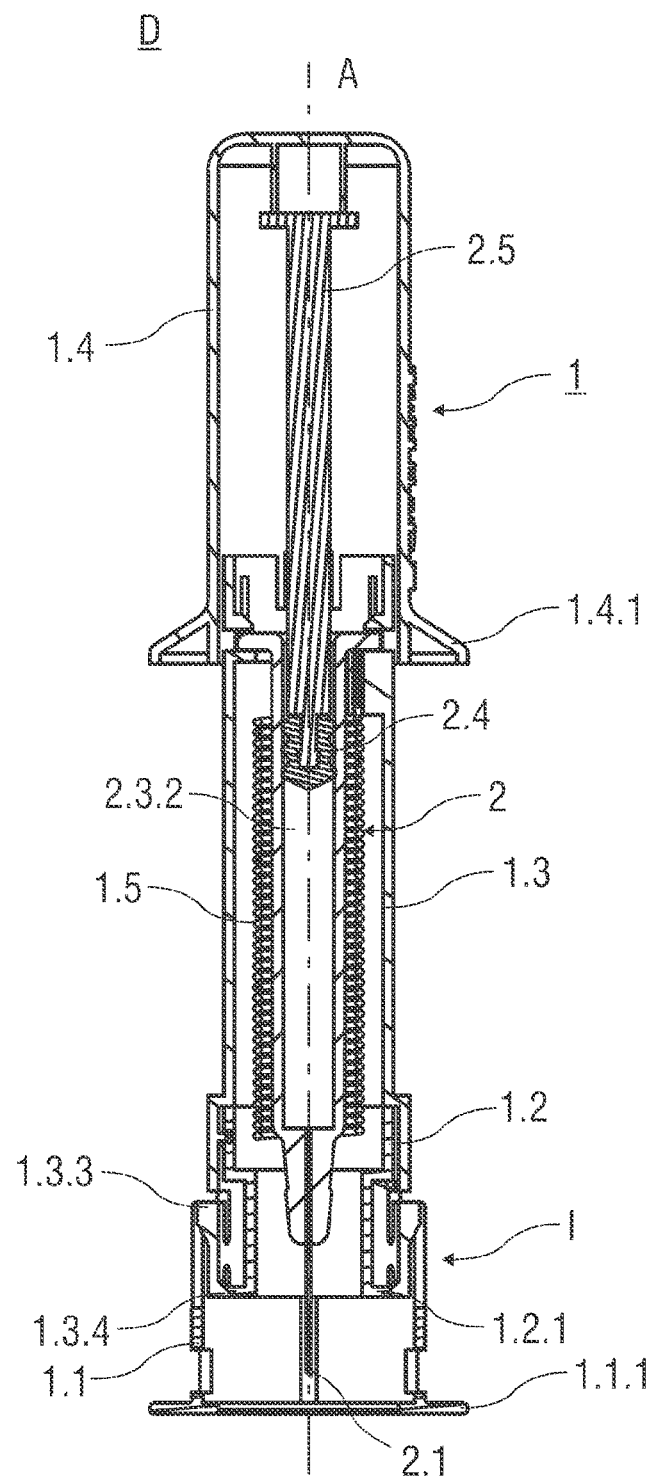

FIGS. 5A and 5B show two sectional views of the injection device D after the needle cap 2.2 has been removed. The sectional view shown in FIG. 5A extends perpendicularly to the one shown in FIG. 5B.

A second protrusion 1.3.3 is formed to the outer surface of the support body 1.3 that engages the first needle shield 1.1 and creates a resistive force to retain the first needle shield 1.1 in the first position I. The second protrusion 1.3.3 extends radially outwards from the support body 1.3 and may flex inwards when the first needle shield 1.1 is moved proximally at the beginning of the injection to uncover the injection needle 2.1. A first catch 1.3.4 is located adjacent to the second protrusion 1.3.3 that projects inwardly and abuts the second flange 1.2.1 of the second needle shield 1.2, so that a distal movement of the second needle shield 1.2 in the retracted position PR is limited.

Alternatively, the first needle shield 1.1 is biased by a plastic spring in the distal direction. The plastic spring may be arranged as a separate part or may be integrally formed to one of the support body 1.3 or the first needle shield 1.1.

Figure 6:
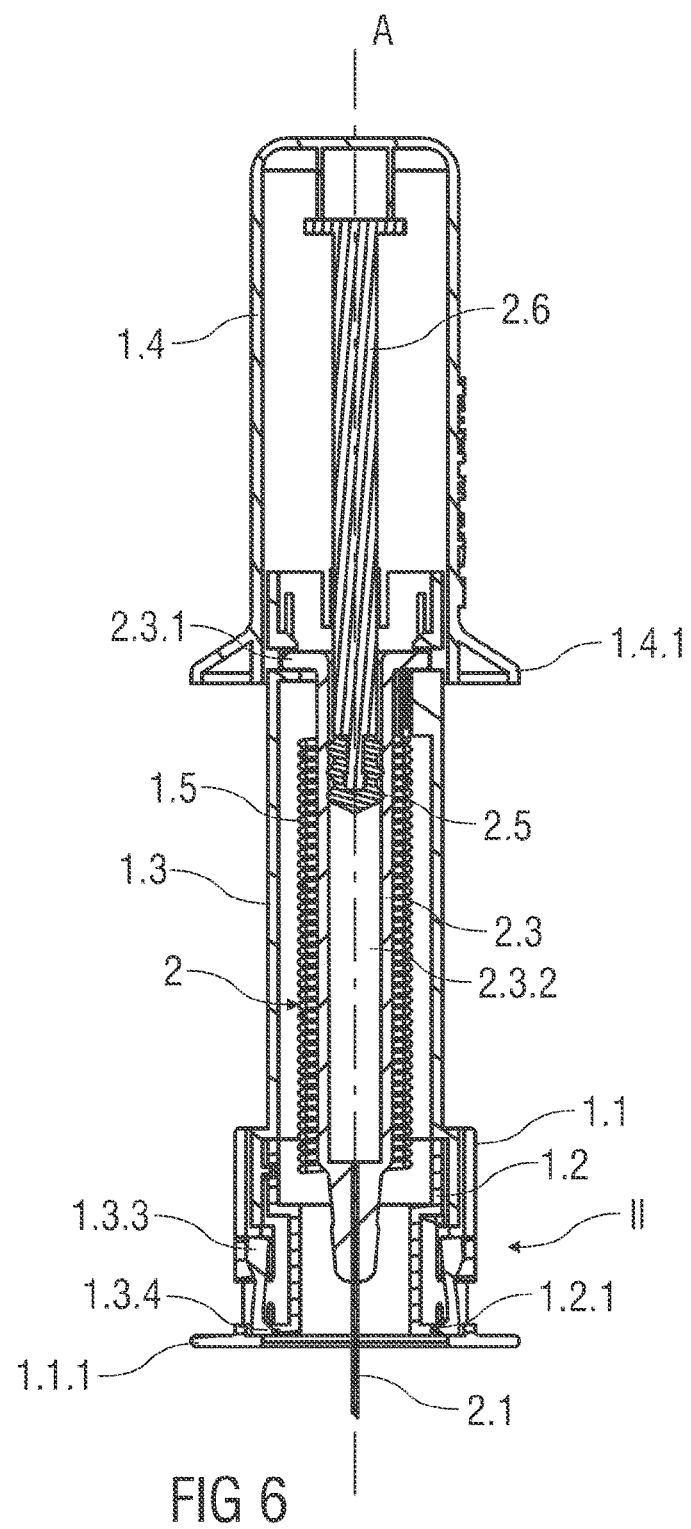
FIG. 6 shows a sectional view of the injection device according to the first embodiment of the invention comprising a first needle shield retracted in a second position.

FIG. 6 shows a sectional view of the injection device D with the first needle shield 1.1 retained in a second position II. The injection needle 2.1 protrudes the second needle shield 1.1 in the distal direction. The second protrusion 1.3.3 bears against an inner surface of the first needle shield 1.1 and is deflected radially inwards, whereby the resulting stress causes the first catch 1.3.4 to flex outwardly, so that the first catch 1.3.4 disengages and releases the second needle shield 1.2.

The dose of medication contained in the pre-filled syringe 2 is administered to the patient as follows: After the needle cap 2.2 is removed from the distal tip of the barrel 2.3, the injection device D is disposed on an injection site, so that the first flange 1.1.1 of the first needle shield 1.1 rests on the skin of the patient.

The first needle shield 1.1 is pushed against the skin surface of the patient and moves from the first position I towards the second position II, whereby the injection needle 2.1 is inserted into the skin of the patient. As the first needle shield 1.1 slides over the support body 1.3, the second protrusion 1.3.3 flexes inwardly, whereby the first catch 1.3.4 is deflected in the radial outward direction to release the second needle shield 1.2.

The pre-tensioned spring means 1.5 partially relaxes and moves the second needle shield 1.2 from the retracted position PR in the distal direction until the second needle shield 1.2 abuts the skin surface of the patient. The safety features of the safety device 1 are now activated.

The outer body 1.4 is pushed towards the skin surface of the patient by a sufficiently large force that allows the first protrusion 1.3.1 to disengage the recess 1.4.2. A further distal movement of the outer body 1.4 with respect to the support body 1.3 translates the plunger 2.6 and the stopper 2.5 in the distal direction, whereby the dose of medication contained in the inner cavity 2.3.2 of the barrel 2.3 is expelled through the injection needle 2.1 and injected.

Figure 7:
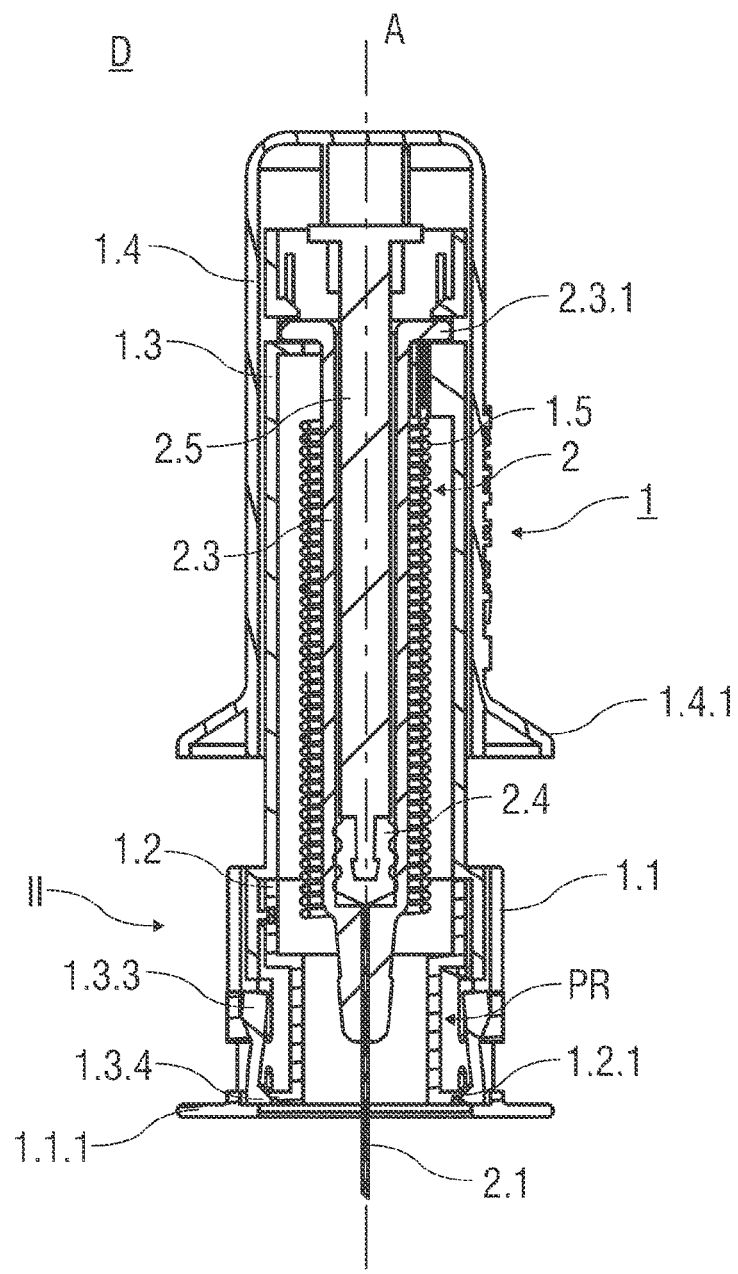
FIG. 7 shows a sectional view of the injection device at the end of an injection stroke.

FIG. 7 shows a sectional view of the injection device D at the end of the injection stroke. The support body 1.3 is substantially received within the outer body 1.4 and the dose of medication has been injected.

The injection device D is removed from the injection site. The spring means 1.5 relaxes and moves the second needle shield 1.2 towards an advanced position PA shown in FIGS. 8A and 8B. The projection 1.3.2 travels within the helical recess 1.2.1 of the second needle shield 1.2 and the second needle shield 1.2 spins around the central axis A. The rotation of the second needle shield 1.2 slows down the distal movement of the second needle shield 1.2 until it reaches the advanced position PA illustrated in FIGS. 8A and 8B.

Figure 8A:
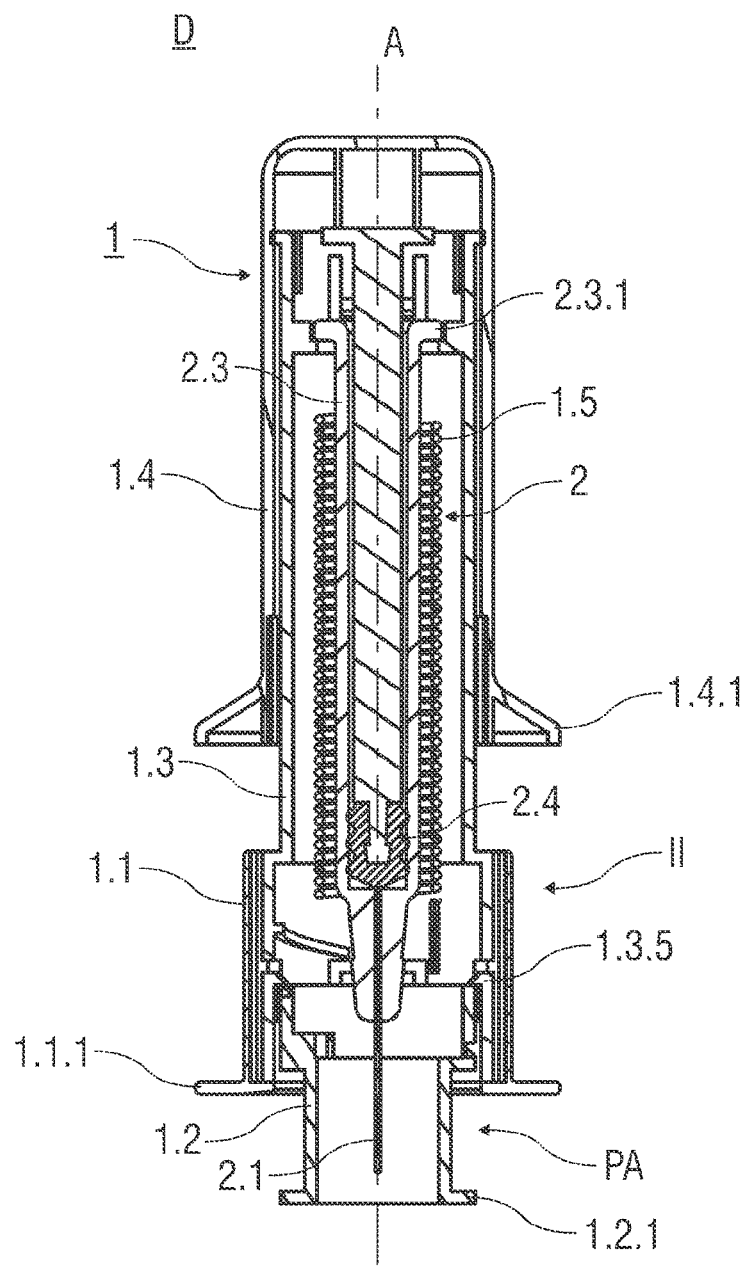
FIGS. 8A and 8B show two different sectional views of the injection device with the second needle shield in an advanced position.
Figure 8B:
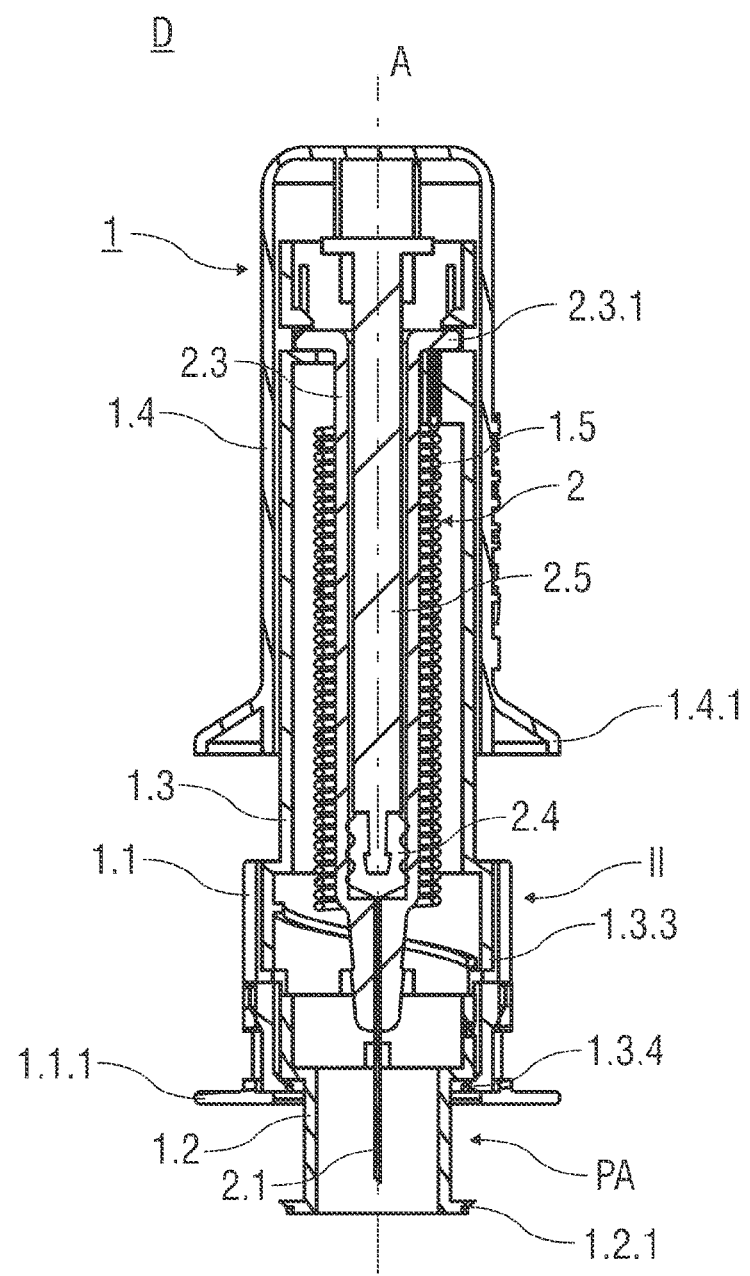

FIGS. 8A and 8B show two different views the injection device D after the injection has been performed and the injection device has been removed from the injection site. The sectional plane shown in FIG. 8A extends perpendicularly to the one shown in FIG. 8B.

The injection needle 2.1 is surrounded by the second needle shield 1.2 in the advanced position PA. As shown in FIG. 8A, a second catch 1.3.5 is formed to the inner surface of the support body 1.3 that latches to the second needle shield 1.2 to prevent a subsequent proximal movement of the second needle shield 1.2 and a re-exposure of the injection needle 2.1.

Respectively, a distal movement of the second needle shield 1.2 with respect to the support body 1.3 is limited by the inwardly projecting first catch 1.3.4. The second needle shield 1.2 is thus permanently locked to the advanced position PA after a single injection has been carried out.

The invention claimed is:

1. A safety device for a pre-filled syringe comprising
a support body adapted to mount the pre-filled syringe,
a first needle shield slidably arranged with respect to the support body and
a second needle shield slidably arranged with respect to the support body and releasably retained in a retracted position (PR), wherein a proximal movement of the first needle shield with respect to the support body releases the retention of the second needle shield in the retracted position (PR), characterized in that the second needle shield comprises a helical recess accommodating a projection of the support body so that the second needle shield is allowed to slide parallel to a central axis (A) of the safety device in the distal direction towards an advanced position (PA) wherein the helical recess is configured to force the second needle shield to rotate with respect to the support body when the second needle shield is allowed to slide parallel to a central axis (A).

2. A safety device according to claim 1, characterized in that the first needle shield comprises a first flange and the second needle shield comprises a second flange, wherein the first and the second flange are adapted to rest on the skin of a patient.

3. A safety device according to claim 1, characterized in that a spring means biases the second needle shield with respect to the support body towards the advanced position (PA).

4. A safety device according to claim 3, characterized in that the spring means is designed as a torsion spring that exerts a torque upon the second needle shield.

5. A safety device according to claim 1, characterized in that the first needle shield is made from an opaque or transparent plastics material and the second needle shield is made from an opaque or transparent plastics material.

6. A safety device according to claim 1, characterized in that an outer body is slidably arranged with respect to the support body, wherein a first protrusion of the support body engages a recess of the outer body to provide a mechanical resistance.

7. A safety device according to claim 1, characterized in that the second needle shield projects distally from the support body in the advanced position (PA) and the support body comprises first and second catches that engage and lock the second needle shield in the advanced position (PA).

8. An injection device (D) comprising a safety device and a pre-filled syringe with an injection needle, wherein the safety device comprises
a support body adapted to mount the pre-filled syringe,
a first needle shield slidably arranged with respect to the support body and
a second needle shield slidably arranged with respect to the support body and releasably retained in a retracted position (PR), wherein a proximal movement of the first needle shield with respect to the support body releases the retention of second needle shield in the retracted position (PR), characterized in that the second needle shield comprises a helical recess accommodating a projection of the support body so that the second needle shield is allowed to slide parallel to a central axis (A) of the safety device in the distal direction towards an advanced position (PA) wherein the helical recess is configured to force the second needle shield to rotate and slide with respect to the support body when the second needle shield is allowed to slide parallel to a central axis (A).

9. An injection device (D) according to claim 8, characterized in that a spring means is capable of moving the second needle shield from the retracted position (PR) to the advanced position (PA), wherein the second needle shield in the advanced position (PA) surrounds the injection needle.

* * * * *